United States Patent
Donohue et al.

(10) Patent No.: US 9,681,808 B2
(45) Date of Patent: Jun. 20, 2017

(54) STIMULATION SYSTEM BASED ON MECHANICAL VIBRATION FOR MODIFICATION AND CHARACTERIZATION OF SLEEP AND BEHAVIOR IN RODENTS

(71) Applicant: Signal Solutions, LLC, Lexington, KY (US)

(72) Inventors: Kevin Donohue, Lexington, KY (US); Bruce O'Hara, Lexington, KY (US); Sridhar Sunderam, Lexington, KY (US); Farid Yaghouby, Lexington, KY (US)

(73) Assignee: Signal Solutions, LLC, Lexington, KY (US)

( * ) Notice: Subject to any disclaimer, the term of this patent is extended or adjusted under 35 U.S.C. 154(b) by 126 days.

(21) Appl. No.: 14/870,286

(22) Filed: Sep. 30, 2015

(65) Prior Publication Data

US 2017/0086673 A1 Mar. 30, 2017

(51) Int. Cl.
*A61B 5/00* (2006.01)
*A61B 5/16* (2006.01)

(52) U.S. Cl.
CPC .............. *A61B 5/0051* (2013.01); *A61B 5/16* (2013.01); *A61B 5/4809* (2013.01)

(58) Field of Classification Search
CPC ......... A61B 5/00; A61B 5/0002; A61B 5/002; A61B 5/0022
USPC ....................................................... 119/421
See application file for complete search history.

(56) References Cited

U.S. PATENT DOCUMENTS

| | | | | |
|---|---|---|---|---|
| 3,803,571 A * | 4/1974 | Luz | ...................... | A61B 5/1105 119/421 |
| 4,437,726 A * | 3/1984 | Lambert | .............. | H01R 13/052 439/825 |
| 4,968,974 A * | 11/1990 | Sakano | .................. | A01K 1/031 119/421 |
| 4,969,417 A * | 11/1990 | Sakano | .................. | A01K 1/031 119/421 |
| 5,044,318 A * | 9/1991 | Sutton | .................. | A01K 5/0241 119/53 |
| 5,868,103 A * | 2/1999 | Boyd | .................... | A01K 15/021 119/719 |
| 6,637,372 B2 * | 10/2003 | Mauderli | ............... | A61B 5/483 119/417 |
| 7,389,744 B2 * | 6/2008 | Zhang | .................... | A01K 1/031 119/421 |
| 8,468,975 B2 * | 6/2013 | Salzmann | .............. | A01K 1/031 119/421 |
| 8,714,113 B2 * | 5/2014 | Lee, IV | ............... | A01K 15/022 119/718 |
| 8,733,290 B2 * | 5/2014 | Gerashchenko | ..... | A01K 29/005 119/421 |

(Continued)

*Primary Examiner* — Richard Price, Jr.
(74) *Attorney, Agent, or Firm* — Stockwell & Smedley, PSC

(57) ABSTRACT

Monitoring behavior of a rodent within a cage includes applying a vibration stimulus to a component of the cage and after applying the vibration stimulus, sensing a signal from a piezoelectric sensor within the cage, the sensed signal indicative of a behavioral response of the rodent. A plurality of attributes of the signal can be determined and the attributes can then be stored in a manner that associates the behavioral response of the rodent with the vibration stimulus.

21 Claims, 6 Drawing Sheets

(56) References Cited

U.S. PATENT DOCUMENTS 8,944,006 B2 * 2/2015 Anderson ................ A01K 5/01
119/51.01

* cited by examiner

STIMULATION SYSTEM BASED ON MECHANICAL VIBRATION FOR MODIFICATION AND CHARACTERIZATION OF SLEEP AND BEHAVIOR IN RODENTS

This invention was made with an award from the Kentucky Cabinet for Economic Development, Office of Commercialization and Innovation, under Grant Agreement KSTC-184-512-13-158 with the Kentucky Science and Technology Corporation. This invention was made with government support under 2R44NS083218 awarded by National Institutes of Health. The government has certain rights in the invention.

BACKGROUND

The present invention relates generally to monitoring rodent behavior and, more particularly, to assessing behavioral response when exposed to a tactile stimulus.

Experiments that manipulate or restrict sleep in rodents and other animals may provide beneficial information related to human sleep disorders. In particular, the experiments can be designed to restrict sleep during different types or stages of sleep. For example, restricting sleep during rapid eye movement (REM) sleep as opposed to non-REM (NREM) sleep may have different effects on physiology and behavior in the period following sleep restriction. Typically, an animal is startled or stimulated in a way that interrupts sleep and then their physiological responses can be monitored. The startle response of an animal may provide useful information for assessing neuropsychiatric disorders and effects of brain injury.

Experimental manipulation of sleep can help with the exploration of how sleep and health may be inter-related and possibly identify new treatments for sleep-related disorders.

Thus, there remains a need to implement selective sleep restriction that is targeted at different stages of sleep with flexible control over the amount, the duration, the timing, and intensity of stimulation that interrupts an animal's sleep. Additionally, measuring a "startle response" of a non-sleeping (or sleeping) animal is desirable as well.

SUMMARY

Embodiments of the present invention relate to a method for measuring movement of a rodent within a cage that includes applying a vibration stimulus to a component of the cage and after applying the vibration stimulus, sensing a signal from a piezoelectric sensor within the cage, the sensed signal indicative of motion and behavior of the rodent. A plurality of attributes of the signal can be determined and the attributes can then be stored in a manner that associates a startle response or any change in behavioral state of the rodent with the vibration stimulus.

Other embodiments relate to a system for measuring movement of a rodent within a cage that includes a vibrating device configured to apply a vibration stimulus to a component of the cage and a piezoelectric sensor within the cage configured to sense a signal, the sensed signal indicative of motion of the rodent after the vibration stimulus is applied. The system also includes a processor and a memory storing executable code accessible by the processor. In particular, the executable code, when executed by the processor, determines a plurality of attributes of the signal and stores the plurality of attributes to associate a startle response or other behavioral state change of the rodent with the vibration stimulus.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not restrictive.

BRIEF DESCRIPTION OF THE DRAWINGS

Various aspects of the present invention are illustrated by way of example, and not by way of limitation, in the accompanying drawings, wherein.

DETAILED DESCRIPTION OF THE PREFERRED EMBODIMENTS

Figure 1:
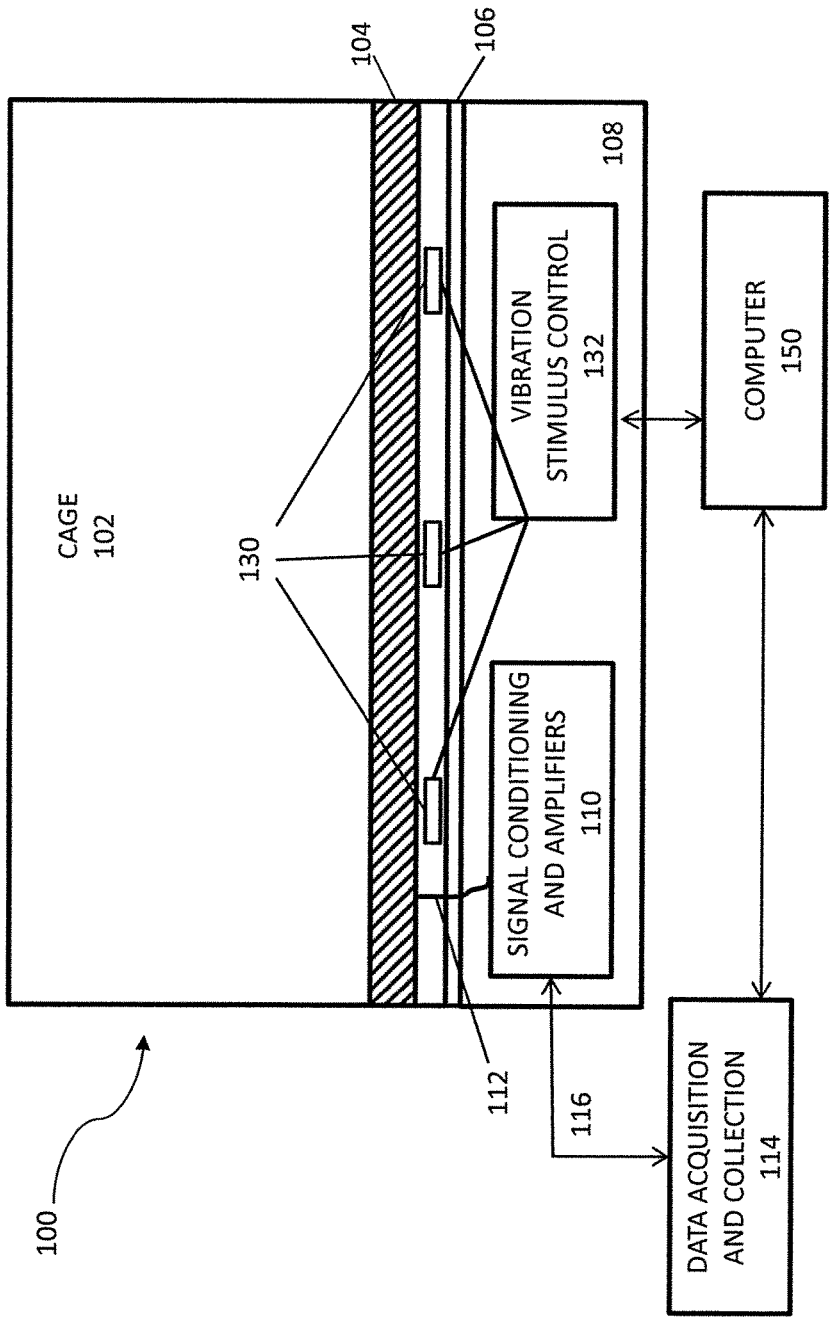
FIG. 1 depicts a block-level diagram of an animal sensing system in accordance with the principles of the present invention.

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

As discussed in more detail below, aspects of the present invention relate to inducing a startle response in a caged animal and measuring that response in a non-invasive manner (e.g., without animal surgery and sensor implants). While a non-invasive method can beneficially be achieved, one of ordinary skill can appreciate that the present system and techniques can be used with more invasive technology as well. Thus, the following description includes a discussion of invasive techniques, non-invasive techniques, and a combination of the two. The startle response is a defensive response to sudden or threatening stimuli. The startle reflex is a brainstem reflectory reaction (reflex) that serves to protect the back of the neck (whole-body startle) and the eyes (eyeblink) and facilitates escape from sudden stimuli. An individual's emotional state may lead to a variety of responses.

In the discussions below, reference may be made to inducing a startle response from a monitored rodent. However, aspects of the present invention relate, more generally, to monitoring the behavior of an animal to a tactile or vibrating stimulus. These techniques can be used to observe behavioral responses while the animal is sleeping, eating, being introduced to a new object in its environment, or having an epileptic seizure. Thus, in additional to inducing a startle response, the stimulus can be used to "distract" the animal during various activities so that its behavioral response can be observed.

Animal models, such as mammalian models in general and rodent models in particular, can be useful in exploring mechanisms of sleep in humans. In particular, information may be discovered about the genetic and/or neurobiological changes underlying sleep abnormalities and other, similar issues. Total sleep deprivation is one method of investigating sleep regulating mechanisms and the effect of sleep loss. However, total sleep deprivation may not be ideal for investigating interrupted sleep, which does not always feature total sleep loss.

Thus, selective sleep deprivation can be investigated as well as total sleep deprivation. Selective sleep deprivation can allow for the comparison of how the different stages of sleep may affect an animal's behavior and cognition. Typically, an electroencephalogram (EEG) can be used to monitor various frequency bands that characterize brain states as a measure of the effect sleep deprivation has on the animal. Electromyography (EMG) may be sensed as well in some embodiments. For example, the frequency band from 0.7 Hz to about 4 Hz is known as slow wave activity and the frequency band from about 6 Hz to about 9 Hz is known as theta activity. One of ordinary skill will recognize that additional bands or different size bands may be monitored and analyzed as well without departing from the scope of the present invention.

There is interest in evaluating the effect of NREM sleep deprivation on either NREM or REM sleep which follows the deprivation. Similarly, the effect REM sleep deprivation has on follow-on REM and NREM sleep can be analyzed as well. However, some techniques for startling an animal awake may be so stressful or stimulating that any observed effects may be due more to the stimulation than merely the sleep interruption. Thus, milder methods of stimulation that selectively interrupt the animal's sleep without over-stimulating or startling the animal are desirable. NREM sleep can be divided into relatively light and deep components that are distinguished by the power in the delta band of the EEG and arousal threshold. Interruption of deep NREM sleep without arousing the animal from NREM sleep may also be of interest in sleep and physiological research.

Accordingly, startling the animal (whether awake or asleep) with controlled amounts of stimulus such that they are awakened without being startled can be beneficial. Inducing the startle response and measuring the startle response to different types and amounts of stimulation can aid in assessing neuropsychiatric disorders and brain injuries. In particular, prepulse inhibition (PPI) is a neurological phenomenon in which a weaker pre-stimulus (prepulse) inhibits the reaction of an organism to a subsequent strong startling stimulus (pulse). The reduction of the amplitude of startle response reflects the ability of the nervous system to temporarily adapt to a strong sensory stimulus when a preceding weaker signal is given to warn the organism. Deficits of prepulse inhibition manifest in the inability to filter out unnecessary information and have been linked to abnormalities of sensorimotor gating. Such deficits are noted in patients suffering from illnesses like schizophrenia and Alzheimer's disease, and in people under the influence of drugs, surgical manipulations, or mutations.

In accordance with the principles of the present invention when stimulating sleeping animals in a closed-loop system, the onset of REM (or NREM) sleep can be detected from analysis of EEG signals of an animal that is caged. This analysis can be performed by personnel observing the EEG signals or can be performed automatically by a computer programmed to recognize patterns in the EEG signal that likely represent the desired stage of sleep is being entered by the animal. Once the animal is determined to be entering REM (or NREM) sleep, then the animal can be partially roused from that sleep stage by stimulation that does not over-startle the animal or completely roused by stimulation that awakens the animal. For example, the stimulation can be transmitted to the animal through the structure of the cage, or some component within the cage, rather than directly applied to the animal's body. In particular, the cage floor can be vibrated at various frequencies, various durations, and in various patterns in order to interrupt the animal's sleep. As one example, a linear solenoid can be vibrated so that one end of a shaft of the solenoid will strike the floor of the animal's cage. One of ordinary skill will recognize that other types of solenoids or actuators may be used that can be controlled to provide desired vibrations to the cage floor or other cage structure (e.g., sides, top, etc.).

As one example, one or more "button-type" shaftless vibration motors (e.g., No. 1638 Pololu Corporation) can be attached under a rubber pad on the floor of the animal's cage. Typically, the motors can be arranged so that a sleeping animal will be near enough to one of the motors to be roused from sleep by the motor's vibration. The example motor identified above vibrates with an amplitude of about 0.75 g at 12,000 RPM when driven by a 3V DC power supply. The vibration is transmitted to the animal's body via the pad and produces tactile stimulation. However, the operation of the vibration motor can be controlled to vary the amplitude of vibration (i.e., measured in "g") and the frequency of the vibration (i.e., measured in Hz or RPM).

In an open loop system, a similar cage and vibrating solenoid arrangement may be used but the application of the stimulus may not be based on the sleep stage of the animal. For example, the vibrating stimulus may be applied periodically during a 4 or 6 hour period. The time between applications of the stimulus can be controlled, the duration of the stimulus can be controlled, the vibrating frequency of the stimulus can be controlled, and the amplitude of the stimulus can be controlled or both the vibrating frequency and amplitude can be modulated (e.g., a ramp function) at the same time. These parameters can be controlled so that a desired startle response is induced in the animal. The application of the stimulus may occur whether or not the animal is in REM sleep, in NREM sleep, or awake.

Thus, one of ordinary skill will recognize that the vibrating stimulus system and techniques described herein may be used in conjunction with an open-loop or closed-loop system and may be related to interrupting sleep in a flexible and selective manner or may be related to inducing a startle response in the caged animal, whether the animal is asleep or awake.

One way to detect or measure the startle response of the animal is to identify sudden movement of the animal. An accelerometer may, for example, be attached to the animal and measurements sent to a data acquisition system so that relatively large changes in the animal's movement can be detected after a vibrating stimulus is applied to the cage. The EEG signals at various frequency bands, or EMG signals, can also provide an indication of the animal's startle response. Alternatively, as a non-invasive technology, a piezoelectric PVDF thin film sensor, such as a mat in the cage (or placed below a mat in the cage), can be used to detect movement of the animal. Such a cage and sensor arrangement is more fully described in U.S. patent application Ser. No. 14/523,994, the entire contents of which are incorporated by reference herein.

In the description below, reference is made to a PVDF sensor by way of example only and one of ordinary skill will recognize that other functionally equivalent sensors can be used without departing from the scope of the present invention.

FIG. 1 depicts a block-level diagram of an animal sensing system in accordance with the principles of the present invention. At the most general level, the system 100 includes a cage 102 for a rodent, for example, that has a sensor 104 for detecting motion of the rodent such as a PVDF sensor. As described in the above-mentioned patent application, there may also be a second, similar sensor which is nearby but isolated from the sensor 104 such that the signals from the two sensors can be combined in such a way as to improve the accuracy of sensing motion of the rodent.

The cage 102 can have a floor to which the sensor 104 is coupled such that rodent-caused vibrations within the cage 102 are transmitted to the sensor 104. The cage 102 and the sensor 104 can rest on a base 108 as well. In addition, a rubber pad, or isolation pad 106, can be located between the sensor 104 and the base 108. The base 108 can be sized and constructed such that electronic circuitry such as signal filters and amplifiers 110 and stimulus control circuitry 132 can be located therein. This signal conditioning circuitry 110 can be connected to the sensor 104 and the stimulus control circuitry 132 can be connected with one or more vibrating solenoids or motors 130 that are located beneath the sensor 104.

In the above-described environment, a rodent in the cage 102 will move (e.g., through breathing, or walking, or grooming, or sleeping) and cause the sensor 104 to generate a signal indicative of the type of motion of the rodent. Furthermore, when startled, the movement of the rodent will cause a relatively large and abrupt change in a signal generated by the sensor 104. This signal is then communicated through the connection 112, which can be a wired or wireless connection, to the amplifier circuitry 110. The resulting amplified signal 116 can then be communicated to a data acquisition and collection system 114.

In the example environment of FIG. 1, the following specific example is provided to aid with understanding underlying principles of the present disclosure. These specific details are but one example of how signals related to the motion of rodents can be accurately obtained.

The PVDF sensor 104 can be sized such that it has a slightly larger footprint than the floor of the cage 102. One example PVDF sensor can be 17.78 cm by 17.78 cm square and have a dielectric with a thickness of about 110 μm. The sensor 104 can be covered by a protective sheet (not shown) and bedding for the animal (not shown) can be placed on the protective sheet.

In an example environment in which the cage 102 is actually multiple cages such that there are a number of sensors near one another, the isolation pad 106 can be used to reduce cross-talk between the different sensors. The pad 106 can, for example, be about 1.6 mm thick, constructed from Shore A 70 Durometer silicon, and extend substantially over the entire top of the base 108 underneath one or more sensors 104.

An example capacitance of the PVDF sensor sheet 104 is approximately 30 nF and when coupled to an input differential amplifier, followed by a low-pass filter, effectively band-pass filters the pressure signals with 3 dB down points at 1.35 Hz and 20 Hz. The differential amplifier provides a high pass effect and can, for example, have a linear gain of about 22. The amplified signals can be fed to a multi-channel data acquisition board (e.g., PCI 6224), sampled at 128 samples per second, and quantized with 16 bits.

Thus, using the environment of FIG. 1, the animal can remain in its home environment and "startle response" experiments and measurements can be conducted without the use of a separate, specialized device or chamber.

Figure 2A:
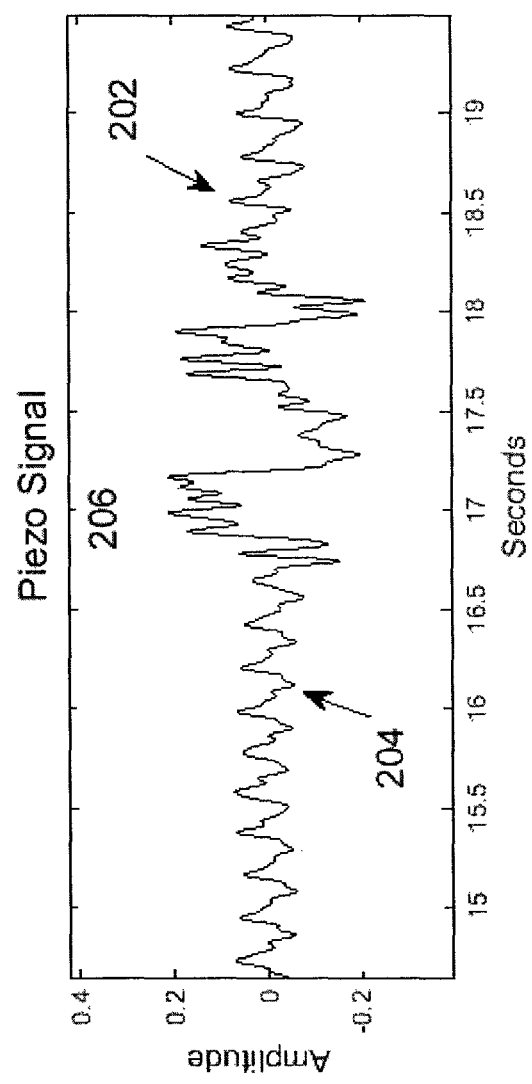
FIG. 2A and FIG. 2B depict two example signals that may be generated by the sensor and the signal conditioning circuitry of FIG. 1.

FIG. 2A depicts an example signal that may be generated by the sensor 104 and the signal conditioning circuitry 110 of FIG. 1. In particular, the signal 202 exhibits a relatively low amplitude periodic signal prior to the point 204. Because the signal 202 is generated by the piezo electric sensor 104, its units of measure can be "volts". However, the amplitude of this signal is indicative of movement or other behavioral changes of the rodent. Movement, respiration rate changes, agitation and other rodent behavior changes will result in variations to the signal generated by the sensor 104. Such a signal 202, of FIG. 2A, would be indicative of NREM sleep of the animal. At the point 204, a vibrating or vibration stimulus can be applied using one or more of the devices 130 described with respect to FIG. 1. The response is motion and weight shifting observed from the larger low frequency amplitude swings starting with the elevation in signal amplitude 206 and ending after about 2 to 3 seconds with the resumption of the low amplitude periodic signal 202, typical of breathing in NREM sleep. A breathing signature is also observed riding on the larger amplitude swings 206, showing an increased breath rate as another temporary response to the stimulus. The time delay from the stimulus to the initiation or peak of the response may also be characteristic of the animal's state or condition. As for the relative amplitude, one or more peaks of the pulse 206 can be about 2 to about 5 times greater (in terms of absolute magnitude) than the NREM signal levels. After the startle response occurs, the signal 202 indicates that the animal returns to NREM sleep.

Figure 2B:
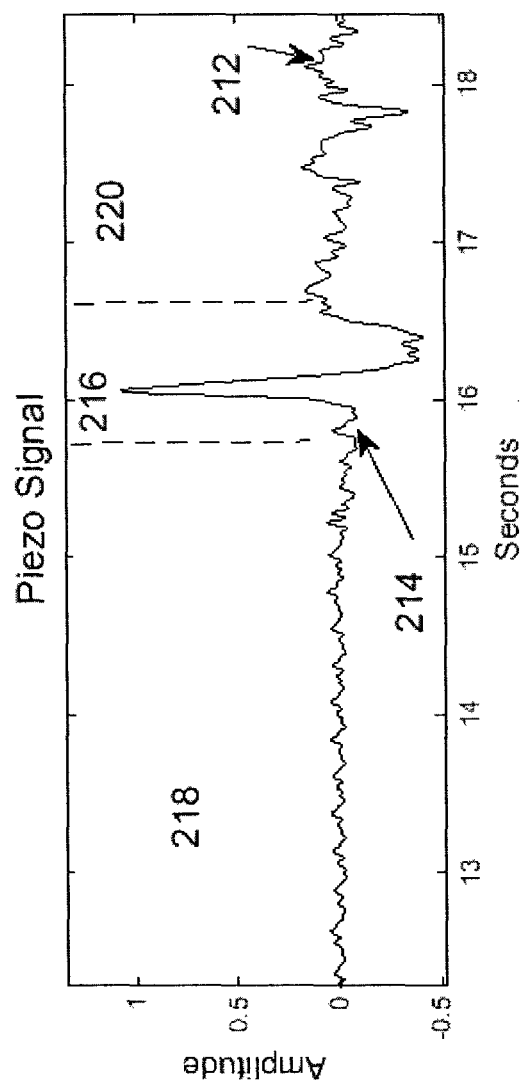

FIG. 2B depicts an alternative example signal that may be generated by the sensor 104 and the signal conditioning circuitry 110 of FIG. 1. In particular, the signal 212, in region 218, exhibits a relatively low amplitude, quasi-periodic signal prior to the point 214. The signal 212 is not as uniformly periodic as the NREM sleep signal of FIG. 2A and more amplitude variation exists as well. The region 218 of the signal 212 corresponds to REM sleep in the animal. At the point 214, a vibration stimulus can be applied using one or more of the devices 130 described with respect to FIG. 1. The resulting pulse 216 captures the startle response of the animal to the vibration stimulus. The width of the pulse 216 can typically be from between about 0.2 s to about 0.4 s. As for the relative amplitude, one or more peaks of the pulse 216 can be about 2 to about 5 times greater (in terms of absolute magnitude) than the average REM signal levels. After the startle response occurs, the signal 212 in the region 220 varies significantly in both amplitude and periodicity. The region 220 of the signal 212 indicates that the animal has awakened.

As shown in FIGS. 2A and 2B, the startle response (e.g., 206, 216) can be detected by the sensor 104 and captured as a time-based signal that has a duration and an amplitude. Similarly, signals from the sensor 104 corresponding to REM and NREM sleep periods have frequency and amplitude characteristics that are different than the startle response signals. By monitoring the values of the signals generated by the sensor 104, the computer 150 can be used to automatically determine the occurrence of a startle response being induced and then capture measurements related to that startle response. Various conventional signal analysis techniques can be utilized by the computer 150 to automatically analyze the signals from the sensor 104 in order to extract information about the startle response of the animal. Additionally, the computer 150 can programmatically control the stimulus control circuitry 132 in order to apply a desired stimulus via one or more of the devices 130. With a priori knowledge (e.g., derived empirically) the computer 150 can determine how much of a delay likely occurs between when the stimulus is applied and when the startle response occurs within the signal from the sensor 104. The computer can merely capture that portion of the signal from the sensor 104 without explicitly analyzing or determining, from signal attributes, that the startle response is occurring.

Animal movement within the cage, whether sleeping, awake, or part of a startle response typically occurs between about 0.5 Hz to about 10 Hz. Thus, the vibrating frequency of the stimulus may be selected outside that range so that the stimulus can be more easily filtered from the signal that indicates motion of the animal. However, as described below, stimulus at about 10 Hz can be utilized if desired.

As mentioned, EEG and EMG signals may be utilized as well in addition to the signals from sensor 104. The EEG and EMG signals may be utilized to help determine a state of sleep (or awakeness) of the animal. These signals may also be monitored as part of the startle response and data collected about them as well. Thus, even though the description of FIG. 3A and FIG. 3B focuses on the detected and measured signals from the sensor 104, EEG and/or EMG signals can be used in addition to or in place of the signals from the sensor 104.

Figure 3A:
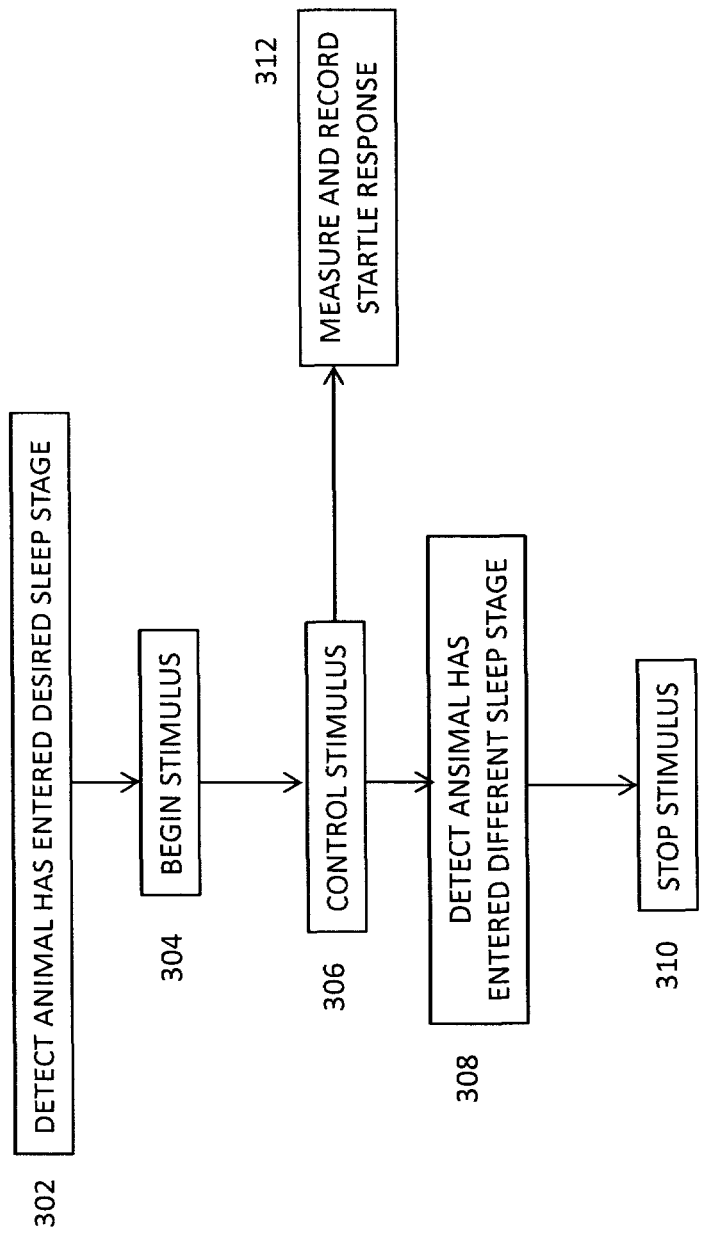
FIG. 3A is a flowchart of an example method for acquiring sensor signals in accordance with the principles of the present invention in a closed-loop system.

FIG. 3A is a flowchart of an example method for acquiring sensor signals in accordance with the principles of the present invention in a closed-loop system. In step 302, a determination is made that the animal has entered a desired sleep stage such as REM sleep, NREM sleep, or awake. As mentioned, this determination can be made using EEG or EMG signals from sensors implanted in the animal. However, the desired sleep stage can also be determined from the vibrations caused by the animal and sensed by the sensor 104 near the floor of the cage. Animal vibrations that occur during REM and NREM sleep tend to occur near a known frequency related to the respiration rate of the animal. Thus, the time between signal peaks can provide an indication that rhythmic breathing is occurring and at what frequency that breathing is occurring. While, an absolute amplitude of the detected signal depends on the specific amplifier circuitry 110 utilized, a relative amplitude difference or ratio between the signals from an awake animal and signals from an asleep animal can be determined (e.g., empirically). Also, signals corresponding to NREM sleep can be distinguished from signals corresponding to REM sleep based on the REM sleep signal exhibiting greater amplitude fluctuations and less uniform periodicity. Accordingly, one of ordinary skill will recognize that automated analysis techniques may be employed to determine, based on the signals from the sensor 104, whether the animal is in a desired sleep stage.

In step 304, the application of the vibration stimulus is begun. The stimulus control circuitry 132 can, for example, vary a voltage that is applied to a vibrating motor (device 130 of FIG. 1) to generate a stimulus. Using conventional motor control techniques, the voltage and timing can be varied so as to control the duration of the stimulus, the frequency of the stimulus and the amplitude of the stimulus.

Thus, in step 306, the stimulus is controlled to provide a stimulus protocol. For example, a single stimulus pulse (of about 0.1 g) with a duration of between 0.5 s to about 1 s can be applied. In the open-loop example described below, for example, a 1 s stimulus pulse (of about 0.2 g) can be applied at 15 minute intervals over the course of 4 to 6 hours when the animal is normally asleep (or awake). The frequency of the stimulus can vary between 8 Hz to about 300 Hz. For example, the frequency of the stimulus can be such that it is outside the hearing range of the animal (which is above 1 kHz for mice) so that only the vibration stimulus is sensed by the animal. Alternatively, the vibrating frequency can be within the hearing range of the animal so that the stimulus has both tactile and aural components. In one example, the vibrating frequency of the stimulus can vary as a ramp function such that over the course of 1 s (or greater) it starts at a lower frequency (e.g., 10 Hz) and linearly climbs to a higher frequency (e.g., 300 Hz). One of ordinary skill will recognize that the stimulus protocols in either a closed-loop or open-loop system can vary greatly without departing from the scope of the present invention. A simple protocol for selective REM sleep restriction with arousal could involve using a mild stimulus (less than 0.1 g at 50 Hz). If the animal adapts to the stimulus, other frequencies can be use (20 Hz, 100 Hz), or the amplitude of the stimulus can be increased up to 0.5 g, at which level the vibration is so large that it could lift the animal off the cage floor. In most cases, a stimulus much lower than this is all that is required for arousal or disruption. For deep sleep restriction without arousal from sleep, a very weak stimulus can be used (less than 0.05 g at 100 Hz) and increased linearly or exponentially in amplitude over a 10 second period to evaluate depth of sleep based on an arousal threshold. For disrupting a wake behavior, such as when a wake theta rhythm is detected, a strong stimulus can be applied (e.g., 0.3 g at randomly selected frequencies over a range of 15 Hz to 300 Hz) to distract the animal during exploratory behavior or novel object interaction.

In step 308, a determination is made that the animal has entered a different sleep stage so that, in step 310, the stimulus can be stopped. Although steps 308 and 312 are shown separately in FIG. 3, they can occur concurrently as well. In particular, in step 312, the startle response of the animal can be detected and measured based on the signal from the sensor 104. In particular, one or more attributes of the startle response can be measured and determined. For example, the maximum and minimum amplitudes may be determined, a duration of the startle response (e.g., the time period between when the stimulus occurs and the animal returns to sleep) may be determined, or Fourier or other frequency-based analysis or deconstruction of the startle response can be performed. These various attributes can be stored for further analysis or correlation with various stimulus signals or pre-pulse signals. In one example, the startle response attributes can be stored in a manner that associates them with the specific stimulus signal that preceded that response.

Figure 3B:
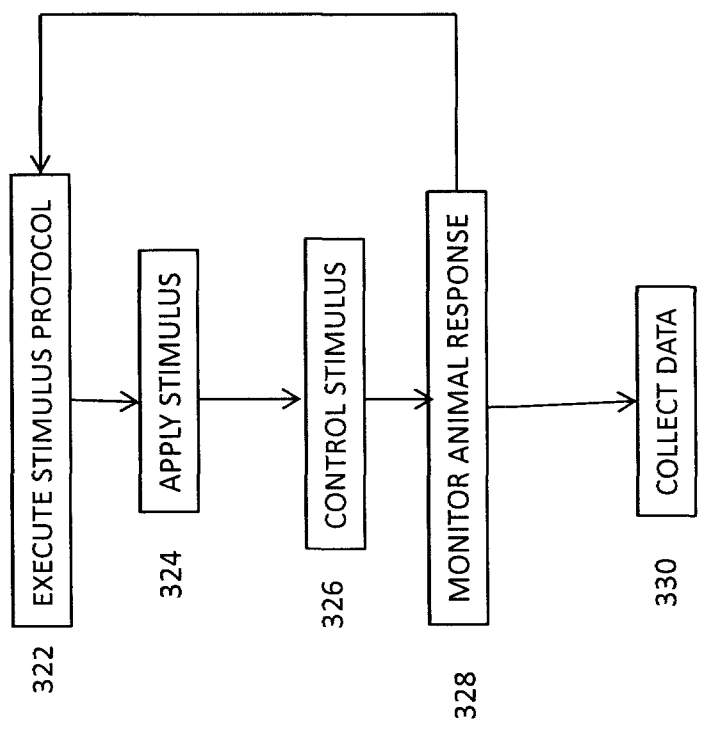
FIG. 3B is a flowchart of an example method for acquiring sensor signals in accordance with the principles of the present invention in an open-loop system.

FIG. 3B is a flowchart of an example method for acquiring sensor signals in accordance with the principles of the present invention in an open-loop system. In this type of system a stimulus protocol can be stored on a storage device of the computer 150 or the stimulus control circuitry 132. The stored stimulus protocol defines the vibrating frequency, the pulse duration, the pulse amplitude and the periodicity of applying the stimulus over a defined time period. Thus, in step 322 the protocol is executed such that the stimulus control circuitry 132 varies the voltage applied to the motors 130 in order to achieve the desired stimulus protocol in step 324. For example, a microcontroller can include a plurality of GPIO pins that, under programmatic control within the microcontroller (e.g., executing stored program code), provide varying voltage signals to one or more of the motors 130 according to the stimulus protocol. Thus, the microcontroller or similar circuitry can control the applied stimulus in step 326.

The startle response of the animal can be monitored and measured in step 328 by capturing the signals from the sensor 104 before, during, and after application of the stimulus. Data about the startle response can then be collected in step 330. The time relationship between the stimulus protocol and the startle response can be determined, for example, by employing a universal clock to synchronize both signals. As mentioned above, PPI may be investigated using the described system and techniques. Thus, the stimulus can include pre-pulses as well as stimulus pulses. Differences in a startle response occurring after the presence or absence of a pre-pulse can then be determined.

Figure 4:
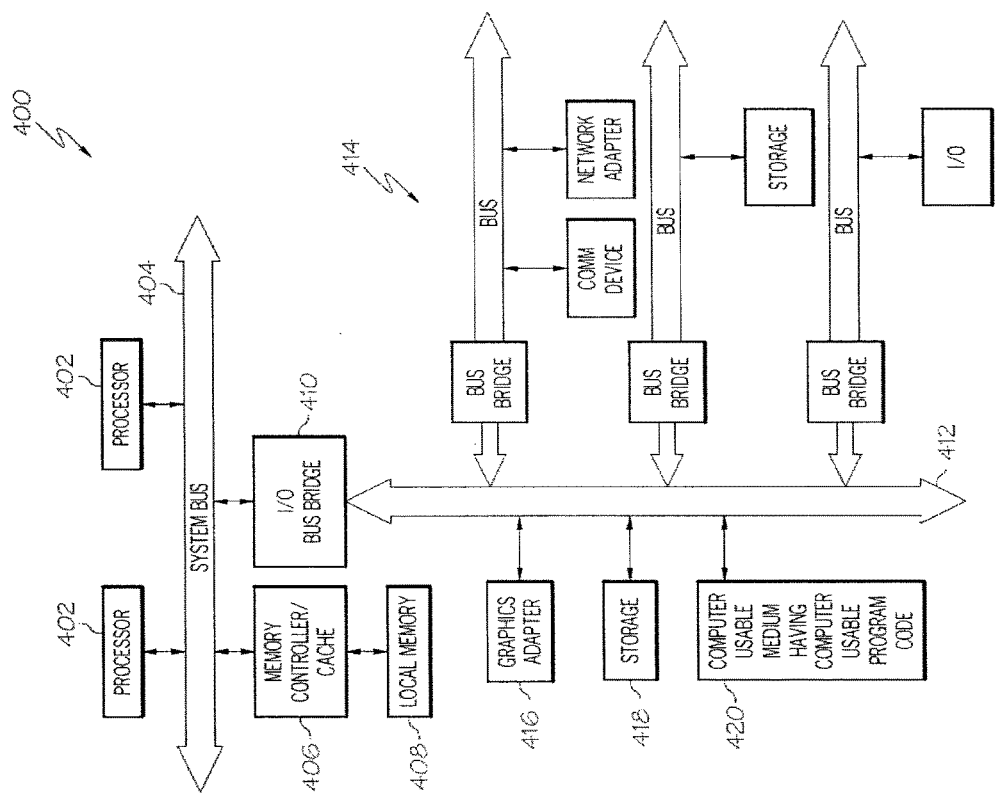
FIG. 4 is a block diagram of a data processing system in accordance with the principles of the present disclosure.

Referring to FIG. 4, a block diagram of a data processing system is depicted in accordance with the present disclosure. A data processing system 400, such as may be utilized to implement the computer or aspects thereof, e.g., as set out in greater detail in FIG. 1-FIG. 3B, may comprise a symmetric multiprocessor (SMP) system or other configuration including a plurality of processors 402 connected to system bus 404. Alternatively, a single processor 402 may be employed. Also connected to system bus 404 is memory controller/cache 406, which provides an interface to local memory 408. An I/O bridge 410 is connected to the system bus 404 and provides an interface to an I/O bus 412. The I/O bus may be utilized to support one or more buses and corresponding devices 414, such as bus bridges, input output devices (I/O devices), storage, network adapters, etc. Network adapters may also be coupled to the system to enable the data processing system to become coupled to other data processing systems or remote printers or storage devices through intervening private or public networks.

Also connected to the I/O bus may be devices such as a graphics adapter 416, storage 418 and a computer usable storage medium 420 having computer usable program code embodied thereon. The computer usable program code may be executed to execute any aspect of the present disclosure, for example, to implement aspects of any of the methods, computer program products and/or system components illustrated in FIG. 1-FIG. 3B. The flowchart and block diagrams in the Figures illustrate the architecture, functionality, and operation of possible implementations of systems, methods and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method for monitoring behavior of a rodent within a cage, comprising:
    applying a vibration stimulus to a component of the cage;
    after applying the vibration stimulus, sensing a signal from a piezoelectric sensor within the cage, the sensed signal indicative of a behavioral response of the rodent;
    determining, by a computer, a plurality of attributes of the signal; and
    storing the plurality of attributes, by the computer, to associate the behavioral response of the rodent with the vibration stimulus.

2. The method of claim 1, wherein the vibration stimulus is applied according to an open-loop stimulus protocol.

3. The method of claim 1, comprising:
    determining, by the computer, when the rodent is in a first sleep state, wherein the vibration stimulus is applied once the rodent is in the first sleep state.

4. The method of claim 3, comprising:
    based on the sensed signal determining, by the computer, when the rodent is in a second sleep state; and
    stopping applying of the vibration stimulus when the rodent is in the second sleep state.

5. The method of claim 1, wherein applying the vibration stimulus comprises:
    energizing a vibrating motor attached proximate to a floor of the cage.

6. The method of claim 5, wherein the vibrating motor is located between a mat and the floor of the cage.

7. The method of claim 1, wherein the vibration stimulus has a frequency between about 8 to 300 Hz.

8. The method of claim 1, wherein the vibration stimulus is applied according to a stimulus protocol that includes a pulse duration, a pulse amplitude, a pulse frequency, and a pulse periodicity.

9. The method of claim 8, wherein the behavioral response is a startle response.

10. The method of claim 1, comprising:
    prior to applying the vibration stimulus, applying a vibration pre-stimulus to the component of the cage, wherein a first amplitude of the pre-stimulus is less than a second amplitude of the stimulus.

11. A system for monitoring behavior of a rodent within a cage, comprising:

a vibrating device configured to apply a vibration stimulus to a component of the cage;

a piezoelectric sensor within the cage configured to sense a signal, the sensed signal indicative of a behavioral response of the rodent after the vibration stimulus is applied;

a processor; and a memory storing executable code accessible by the processor, wherein, when executed by the processor, the executable code:

determines a plurality of attributes of the signal; and stores the plurality of attributes to associate the behavioral response of the rodent with the vibration stimulus.

12. The system of claim 11, wherein applying the vibration stimulus comprises:

energizing a vibrating motor attached proximate to a floor of the cage.

13. The system of claim 12, wherein the vibrating motor is located between a mat and the floor of the cage.

14. The system of claim 11, wherein the vibration stimulus is applied according to an open-loop stimulus protocol.

15. The system of claim 11, wherein, when executed by the processor, the executable code:

determines when the rodent is in a first sleep state, wherein the vibration stimulus is applied once the rodent is in the first sleep state.

16. The system of claim 15, wherein, when executed by the processor, the executable code:

determines, based on the sensed signal, when the rodent is in a second sleep state; and stops applying the vibration stimulus when the rodent is in the second sleep state.

17. The system of claim 11, wherein the vibration stimulus has a frequency between about 8 to 300 Hz.

18. The system of claim 11, wherein the vibration stimulus is applied according to a stimulus protocol that includes a pulse duration, a pulse amplitude, a pulse frequency, and a pulse periodicity.

19. The system of claim 11, wherein the vibrating device comprises:

a plurality of vibrating devices, each attached to a respective location on the cage.

20. The system of claim 11, wherein the vibrating device is further configured to apply, prior to applying the vibration stimulus, applying a vibration pre-stimulus to the component of the cage, wherein a first amplitude of the pre-stimulus is less than a second amplitude of the stimulus.

21. The system of claim 11, wherein the behavioral response is a startle response.

* * * * *